(12) United States Patent
Jensen et al.

(10) Patent No.: US 7,658,540 B2
(45) Date of Patent: Feb. 9, 2010

(54) IMAGING ASSEMBLY STABILIZATION DEVICE AND METHOD OF USE

(75) Inventors: Vernon Thomas Jensen, Draper, UT (US); Lonnie B. Weston, Syracuse, UT (US); David Barker Ellis, Salt Lake City, UT (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/622,368

(22) Filed: Jan. 11, 2007

(65) Prior Publication Data

US 2008/0170669 A1 Jul. 17, 2008

(51) Int. Cl.
*H05G 1/02* (2006.01)
(52) U.S. Cl. ........................ 378/197; 378/198
(58) Field of Classification Search .......... 378/196–198
See application file for complete search history.

(56) References Cited

U.S. PATENT DOCUMENTS

| | | | | |
|---|---|---|---|---|
| 5,448,607 A | * | 9/1995 | McKenna | 378/4 |
| 6,132,087 A | * | 10/2000 | Kusch et al. | 378/197 |
| 6,431,751 B1 | * | 8/2002 | Everett et al. | 378/197 |
| 6,456,684 B1 | * | 9/2002 | Mun et al. | 378/20 |
| 2002/0168044 A1 | * | 11/2002 | Tybinkowski et al. | 378/4 |

\* cited by examiner

*Primary Examiner*—Hoon Song
(74) *Attorney, Agent, or Firm*—McAndrews, Held & Malloy, Ltd.; Peter J. Vogel; Michael A. Dellapenna

(57) ABSTRACT

Certain embodiments provide systems and methods for gantry support. Certain embodiments provide a mobile imaging system. The system includes a base and a gantry member moveably attached to the base. The gantry member includes an imaging source. The system also includes a gantry support positioned on the base for supporting the gantry member. The gantry support contacts the gantry member at one or more points in a range of motion for the gantry member. Certain embodiments provide a method for gantry member stabilization. The method includes providing a gantry support on a gantry base to provide support for an imaging system gantry member. The imaging system gantry member is attached to the gantry base. The method further includes positioning the gantry support with respect to the gantry member to support the gantry member along at least a portion of a path of movement of the gantry member.

18 Claims, 11 Drawing Sheets

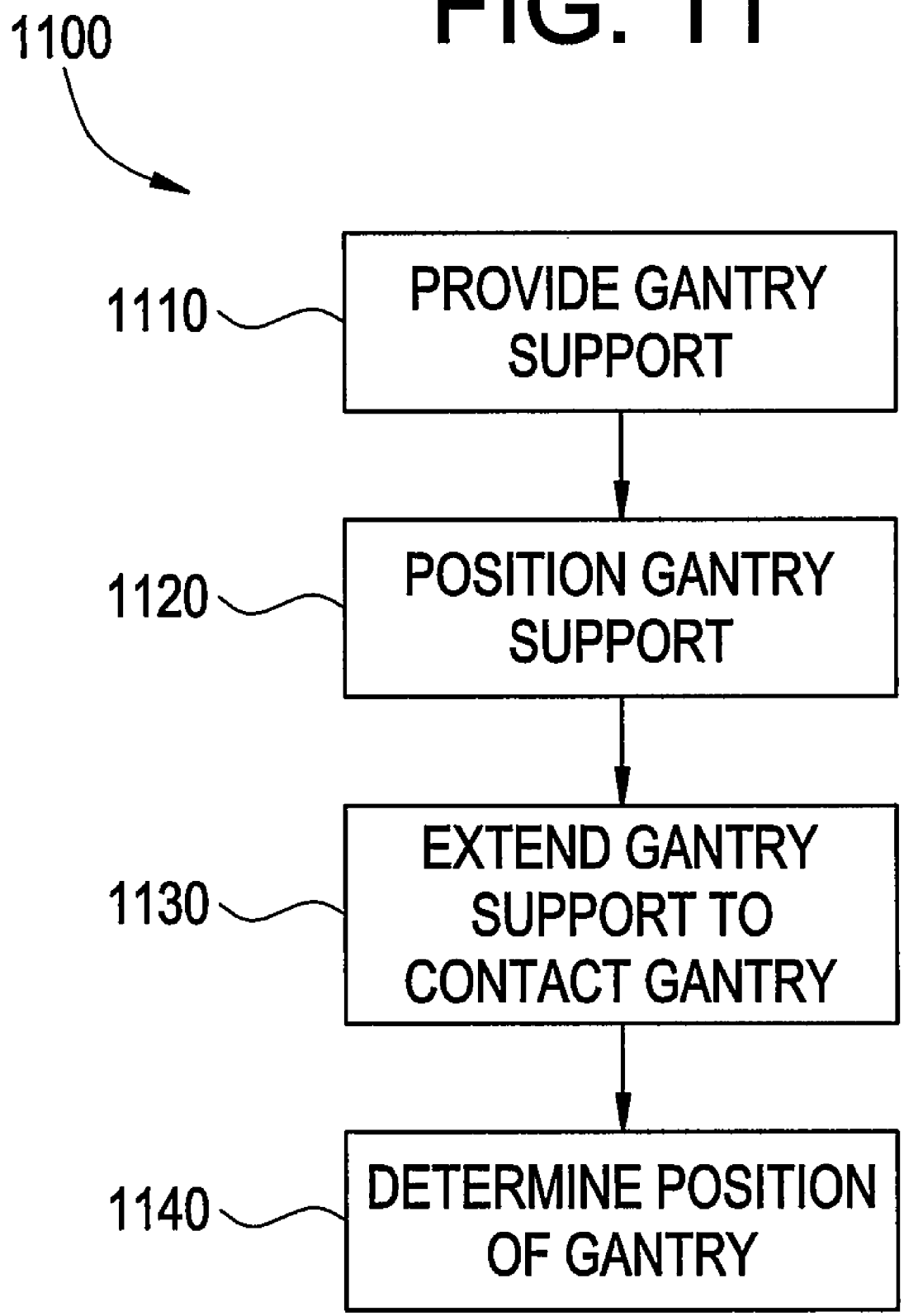

IMAGING ASSEMBLY STABILIZATION DEVICE AND METHOD OF USE

BACKGROUND OF THE INVENTION

The present invention generally relates to imaging systems. More specifically, certain embodiments of the present invention related to stabilization devices for mobile imaging.

Mobile fluoroscopic X-ray systems are used in a variety of clinical environment, such as hospital radiology and surgery departments. A mobile C-arm configuration is a popular configuration for such imaging systems. Recent improvements in motorization, imaging, image processing and visualization have led to a newer generation of C-arms that can acquire images from multiple angle projections to reconstruct 'CT like' three-dimensional (3D) data sets. These 3D mobile C-arms provide operators an option of intra-operative 3D imaging, as well as two-dimensional (2D) imaging.

Although mobile 3D C-arms have been available for at least four years, the technology has not gained wide acceptance due to system workflow and image quality deficiencies. One advantage that 'fixed room' systems have over mobile platforms is a ridged mechanical gantry that is secured to a floor or ceiling. A benefit obtained by utilizing a ridged gantry is positional accuracy with few weight limitations typically associated with mobile systems. Precise positioning translates into accurate reconstructions and better 3D reconstruction accuracy and image quality.

A mobile C-arm's positioning flexibility and maneuverability are positive attributes in most imaging applications, but result in mechanical variation and non-repeatable motion that becomes a liability during a 3D image 'scan'.

In an attempt to improve mobile 3D image quality, one company has introduced a mobile system that fully encloses the rotational gantry into an 'O' shape. While the O-shaped gantry increases a 3D scan range beyond a typical 190 degrees, the O-shaped gantry arm also adds significant weight to a weight sensitive point on the gantry structure. For example, the 'O gantry' weights over 1600 lbs compared to 700 lbs for a traditional C-arm. As a result of the 'O' shaped gantry and increased system weight, positioning flexibility, maneuverability, and product cost of this systems suffer.

Many factors may negatively affect mobile gantry precision. For example, mobile C-arm gantries may be affected by C-flex, C-oscillation and loose mechanical interfaces having motorized parts and articulated joints. Oscillation and flex occur in both 2D and 3D imaging and blurring may result in 2D and 3D images.

Thus, there is a need for systems and methods for improved stabilization of mobile C-arm and other gantries.

BRIEF SUMMARY OF THE INVENTION

Certain embodiments provide systems and methods for gantry support. Certain embodiments provide a mobile imaging system. The system includes a base and a gantry member moveably attached to the base. The gantry member includes an imaging source. The system also includes a gantry support positioned on the base for supporting the gantry member. The gantry support contacts the gantry member at one or more points in a range of motion of the gantry member.

Certain embodiments provide a method for gantry stabilization. The method includes providing a gantry support on a gantry base to provide support for an imaging system gantry member. The imaging system gantry member is attached to the gantry base. The method further includes positioning the gantry support with respect to the gantry member to support the gantry member along at least a portion of a path of movement of the gantry member.

Certain embodiments provide an imaging assembly stabilization system. The system includes an imaging assembly moveably attached to a base. The system also includes an imaging assembly support positioned on the base. The imaging assembly support is configured to contact the imaging assembly to stabilize the imaging assembly at one or more points along an orbital path of the imaging assembly.

BRIEF DESCRIPTION OF SEVERAL VIEWS OF THE DRAWINGS

FIG. 11 illustrates a flow diagram for a method for stabilizing an imaging system gantry in accordance with an embodiment of the present invention.

Figure 1:
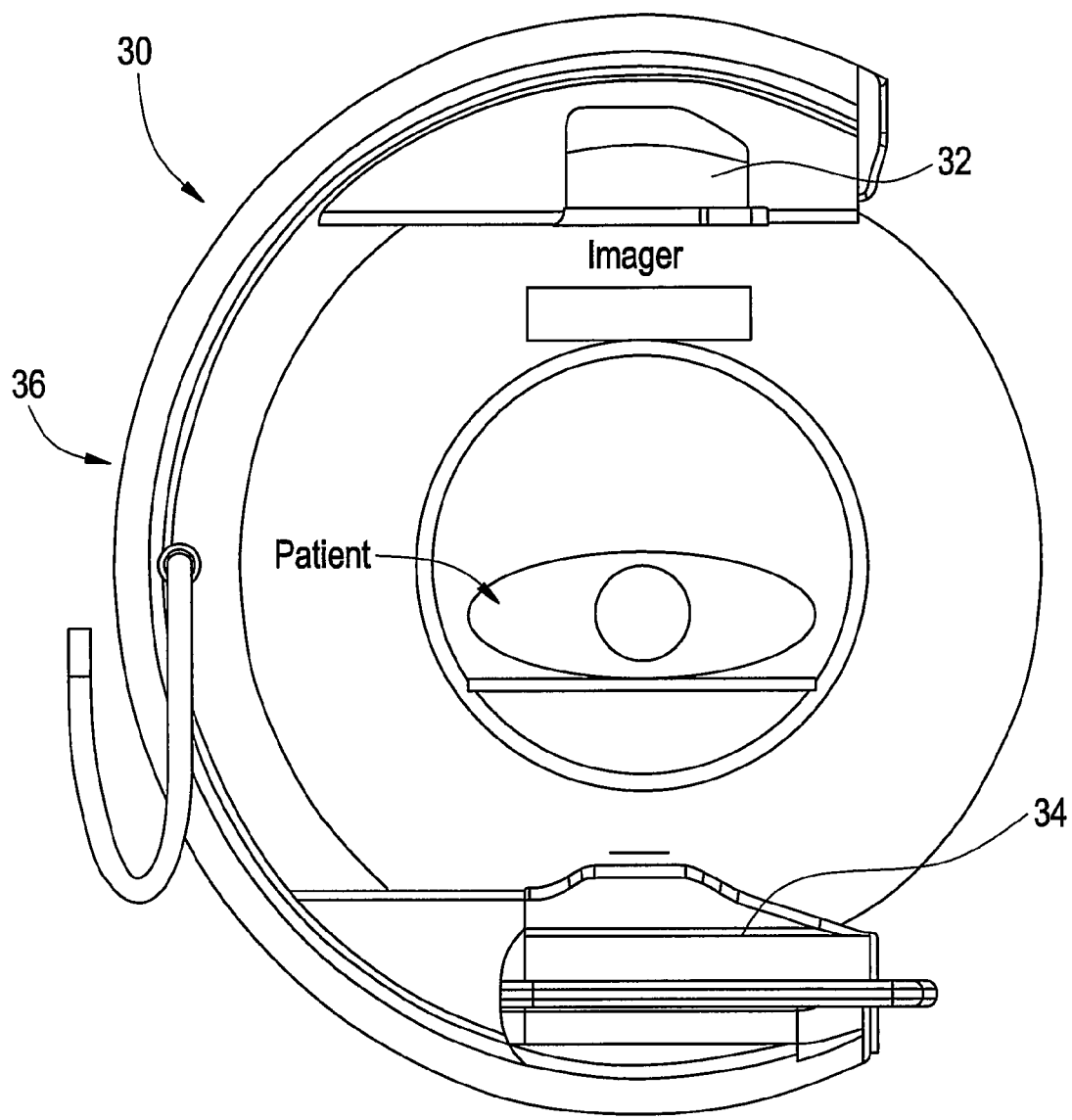
FIG. 1 illustrates an exemplary imaging system for use in an operating room environment.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Certain embodiments provide improved stabilization in an imaging system. Certain embodiments provide additional support to a gantry in an imaging system. As used herein, a gantry is defined as having at least a support member assembly, such as a C-shaped support arm (or "C-arm"), an L-shaped support arm, an O-shaped support arm, etc., and a gantry base to which the support assembly is attached (often moveably attached). The support member or imaging assembly includes an imaging detector and imaging source on the support member, for example. The support member/imaging assembly is moveably attached to the base such that the support member is positionable and/or otherwise moveable on the gantry base, for example. Certain embodiments add an additional support or point of contact at an end of a gantry base to improve gantry stability. While certain embodiments apply to a plurality of gantry or imaging assembly designs, certain embodiments are discussed below in relation to C-arm systems for purposes of illustration only.

A gantry or imaging assembly may be used in an imaging system to position an imaging source and an imaging receptor. FIG. 1 illustrates an exemplary imaging system 10 for use in an operating room environment. As shown in FIG. 1, the camera system 10 includes an imager 12, a camera source 14, and a structural support member 16. The imager 12 may be an x-ray detector, for example. The camera source 14 may be an X-ray generator, for example. Although depicted in FIG. 1 as a C-arm, the structural support member 16 may be any of a variety of gantries and/or other structure supporting the imager 12 and source 14.

For example, the imager 12 may be mounted on the structural support member 36 opposite the camera source 14. The support member 16 moves about a patient or other object to produce two dimensional projection images of the patient from different angles. The patient or object remains positioned between the imager 12 and the source 14, and may, for example, be situated on a table or other support, although the patient/object may move.

In an embodiment, the system 10, such as a fluoroscope system, operates with the imager 12 positioned opposite the X-ray source or generator 14. While in some systems, the imager 12 is fixed overhead and the source 14 is located below a patient support, the discussion below will be illustrated with regard to the more complex case of a typical C-arm fluoroscope, in which the imager or detector 12 and source 14 are connected by the structural support member 16, such as a C-arm, that allows movement of the imager 12 and camera source assembly 14 about the patient so that the C-arm may be positioned to produce x-ray views from different angles or perspectives. In such C-arm devices, the imaging beam generally diverges at an angle, the relative locations and orientations of the imager 12 and source 14 vary with position due to structural flexing and mechanical looseness, and the position of both the imager 12 and the source 14 with respect to the patient and/or a tool which it is desired to track may also vary in different shots.

Figure 2:
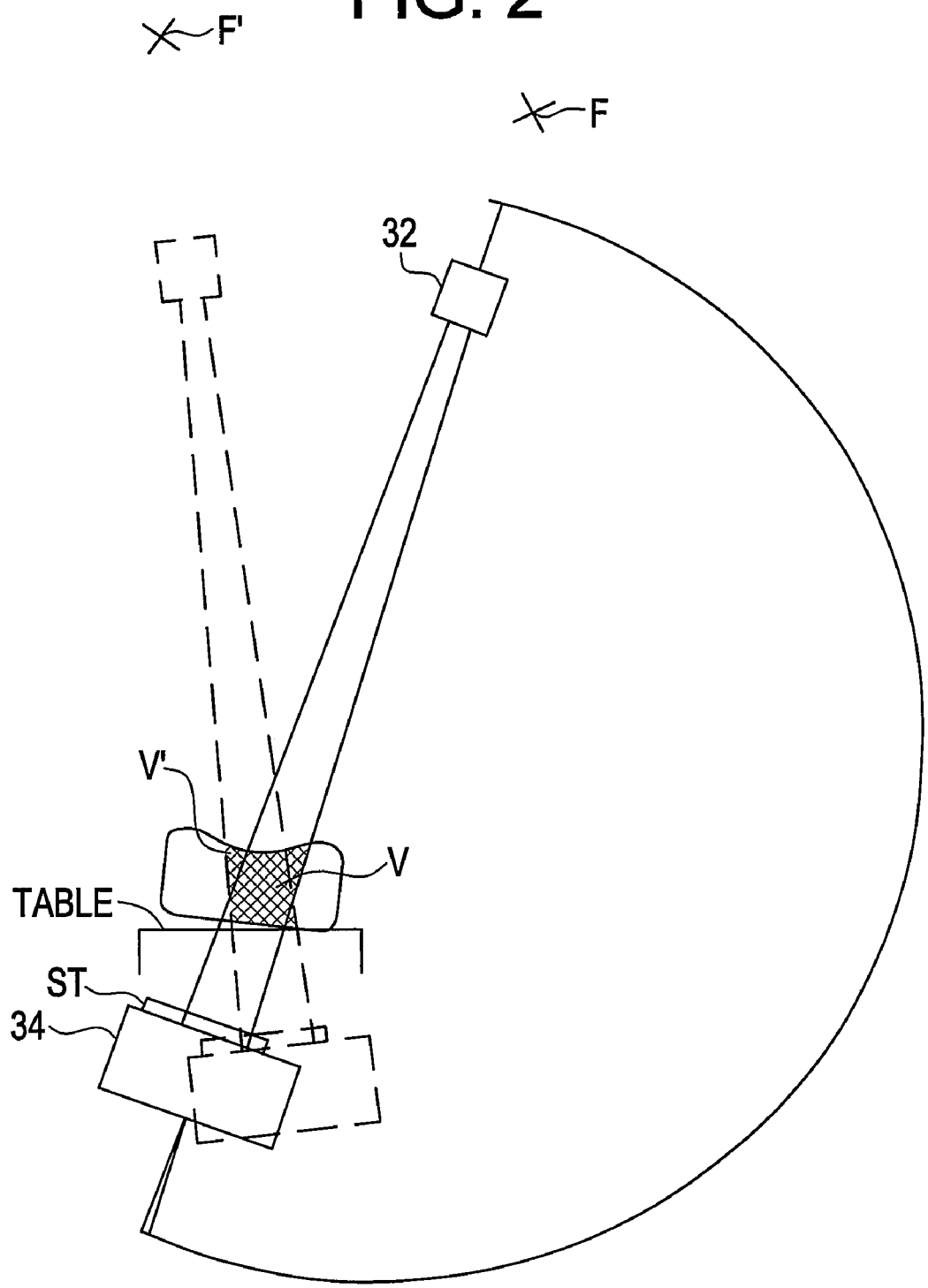
FIG. 2 illustrates an exemplary C-arm imaging system in two different imaging positions.

FIG. 2 illustrates the system 10 in two different imaging positions, with a first position shown in solid line, and a second position in dashed line phantom. In the first position, a tissue volume V is imaged with a divergent beam from the above right, and a virtual beam origin or focal point at F, while the image from the second position catches a largely overlapping but partly distinct tissue volume with a divergent beam from the upper left, and a different focal point F'. The distances from points F, F' to the camera may be different, and the camera itself may shift and tilt with respect to the beam and its center axis, respectively.

In practice, the x-ray beam is generally aimed by its center ray, whose intersection with the imaging plane, referred to as the piercing point, may be visually estimated by aiming the assembly with a laser pointing beam affixed to the source. The x-ray beam may be considered to have a virtual origin or focal point F at the apex of the cone beam. Generally, the imager assembly 12 is positioned close to the patient, but may be subject to constraints posed by the operating table, the nature of the surgical approach, and tools, staging, clamps and the like, so that imaging of a tissue volume somewhat off the beam center line, and at different distances along the beam, may occur.

As noted above, flexing of the C-arm or other support member 16 changes the distance to the focal point F and this also may slightly vary the angular disposition of the beam to the camera source 14, so this shifting geometry may affect the fluoroscope images. Deflection or physical movement of the camera itself, as well as electron/optical distortion from the camera geometry, image detector and variations due to gravitational, magnetic or electromagnetic fields, may enter image reception and affect projective geometry and other distortion of a final image produced by the assembly.

Figure 3:
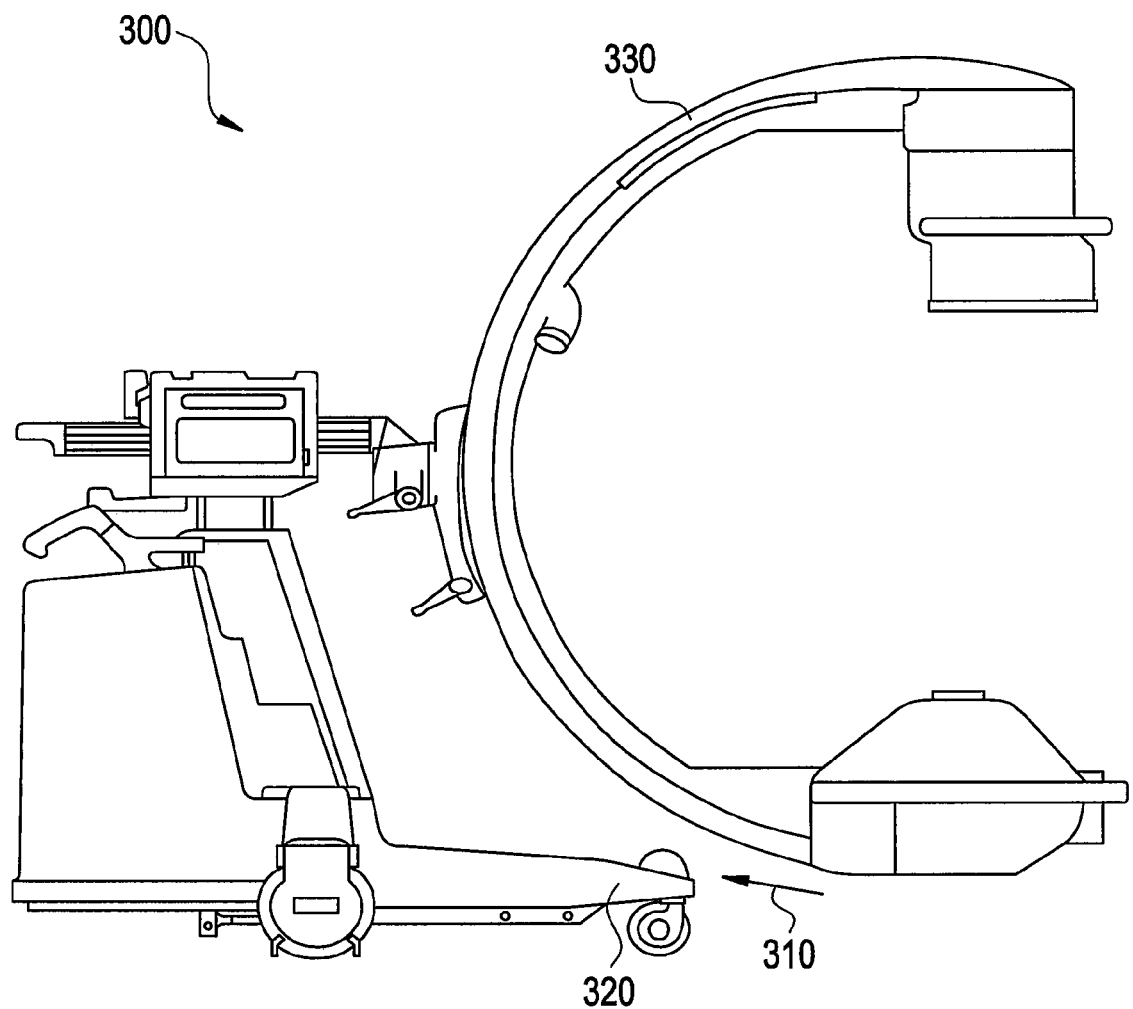
FIG. 3 illustrates a stabilization roller positioned on a C-arm base in accordance with an embodiment of the present invention.
Figure 4:
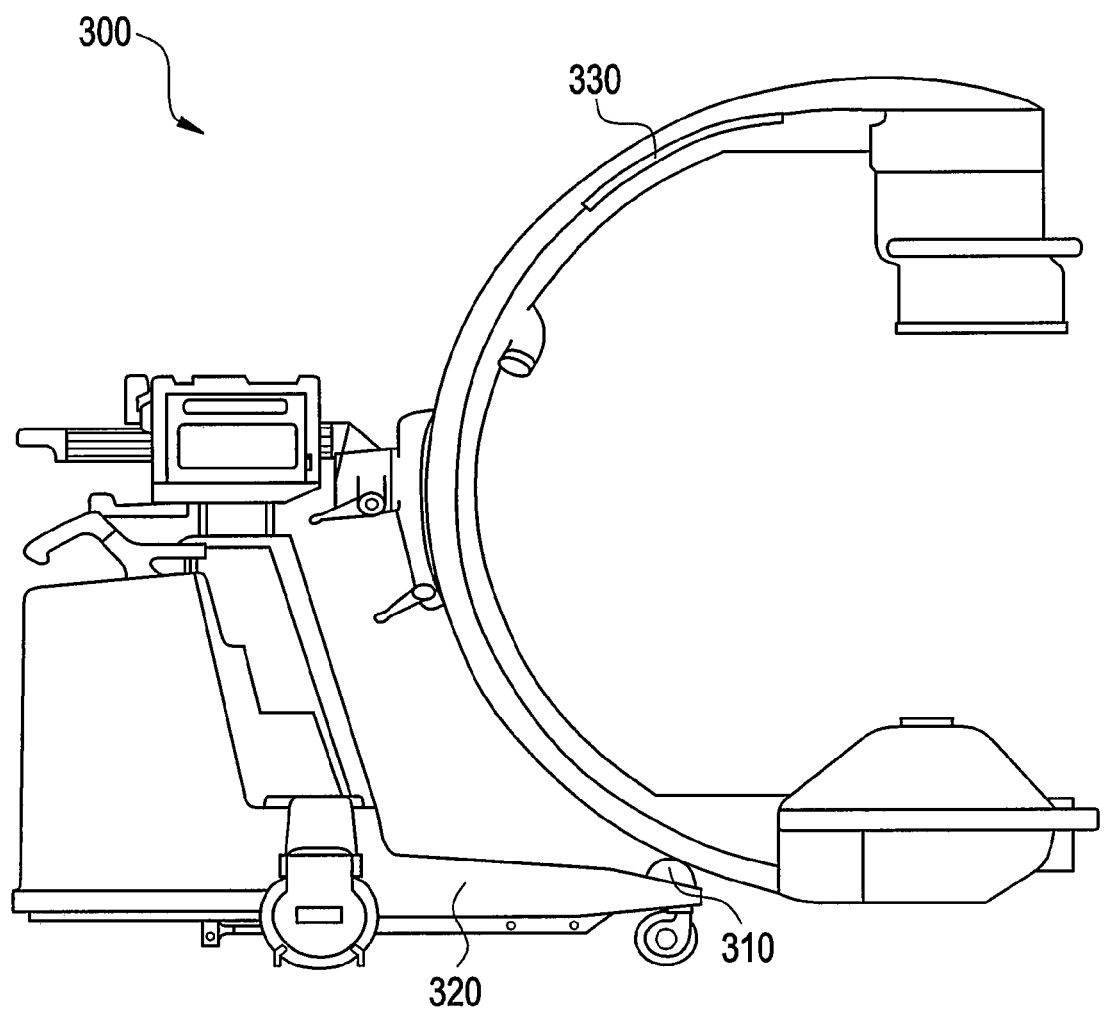
FIG. 4 illustrates a docked x,y position (anterioposterior (AP) orbital position) of a C-arm system including a roller assembly in accordance with an embodiment of the present invention.

FIG. 3 illustrates a stabilization roller 310 positioned on a C-arm 'toe' 320, where the C-arm 330 is in a non-docked x,y position (an anteroposterior (AP) orbital position), for example. In certain embodiments, such as the embodiment shown in FIG. 3, a roller assembly 310 is added to the C-arm gantry or other imaging assembly at the base or toe 320. The roller assembly 310 may include one or more rollers of a material that can help provide easy movement of the C-arm 330 or other imaging assembly, for example. When the C-arm 330 is in a 'x,y, home' position, the roller assembly 310 makes contact with the C-arm 330 through most of the arm's orbital rotation (see FIG. 4). FIG. 4 illustrates a docked x,y position (AP orbital position) of the C-arm system including the roller assembly 310.

Figure 5:
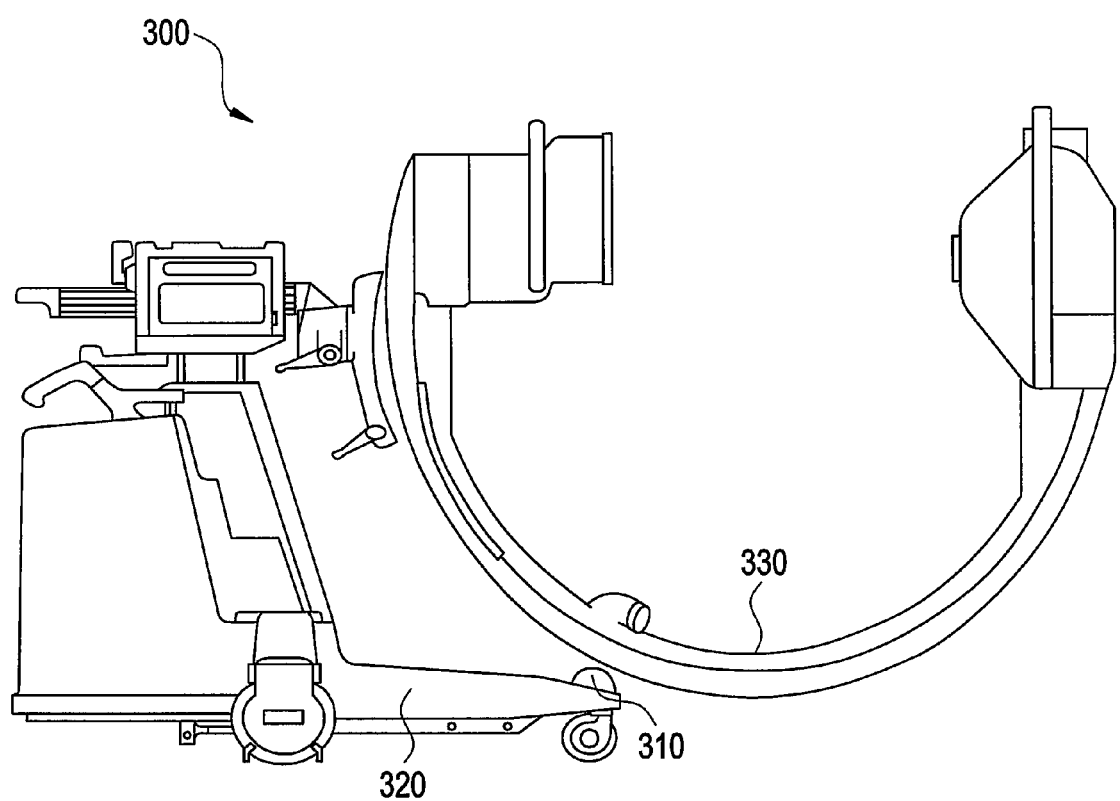
FIG. 5 illustrates a docked x,y position of a C-arm in a lateral orbital position in accordance with an embodiment of the present invention.

During a portion of the orbital travel where the roller 310 makes contact with the C-arm 330, flex and oscillation may be reduced, for example. FIG. 5 illustrates a docked x,y position of the C-arm 330 in a lateral orbital position. As shown in FIG. 5, for example, the roller assembly 310 helps reduce flex and oscillation at a fully extended AP position.

Figure 6:
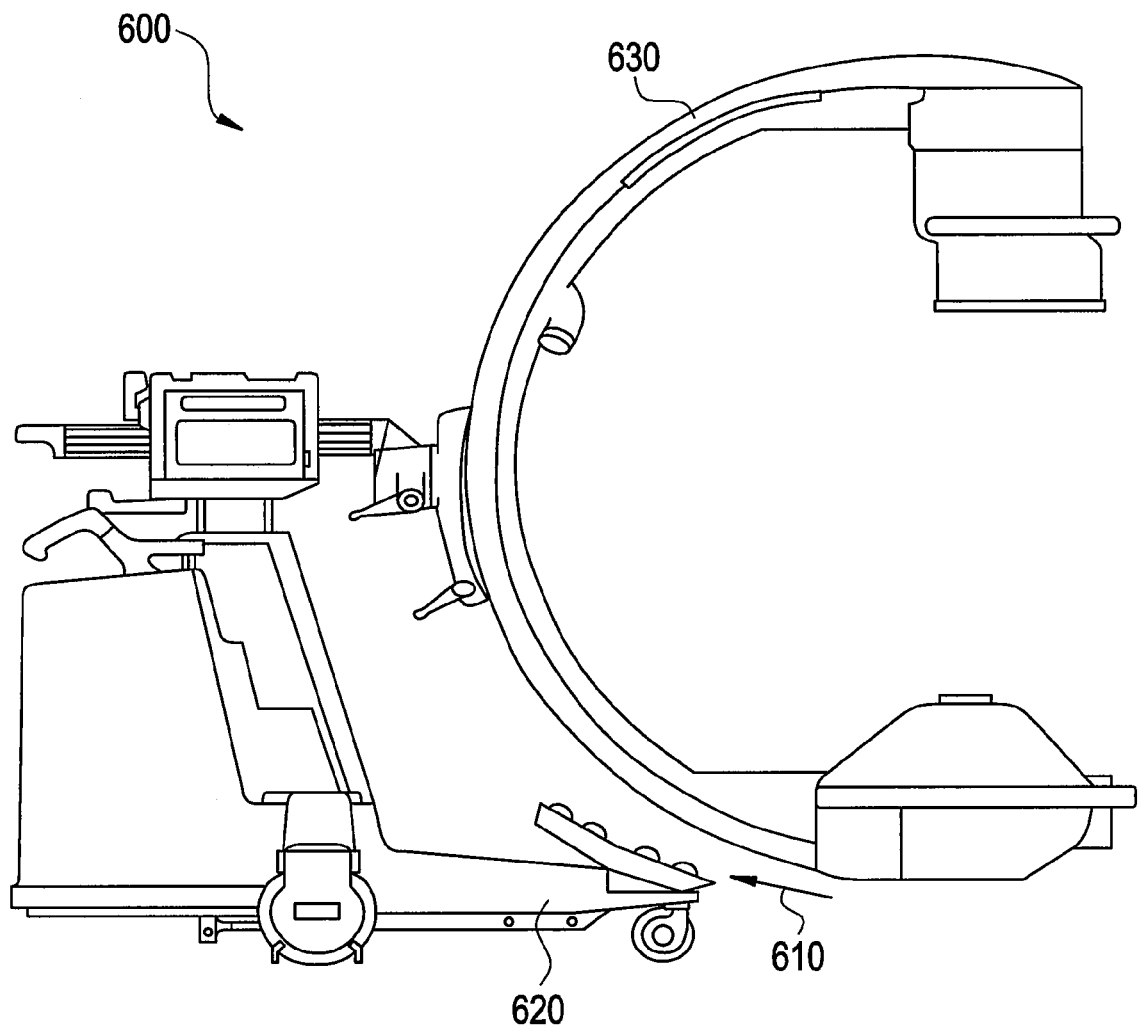
FIG. 6 illustrates an imaging system including a stabilization truck assembly on a C-arm toe in an AP orbital, non-docked x,y position in accordance with an embodiment of the present invention.

FIG. 6 illustrates an imaging system 600 including a stabilization 'truck' assembly 610 on a C-arm 'toe' 620 in an AP orbital, non-docked x,y position. Certain embodiments include multiple rollers arranged in a 'truck assembly' 610, such as the C-arm system 600 shown in FIG. 6. The truck assembly 610 may include one or more rollers or other moveable objects of a material that can help provide easy movement of the C-arm 630 or other imaging assembly, for example. The truck assembly 610 may add stability through a greater portion of the C-arm 630 orbital range of motion.

Figure 7:
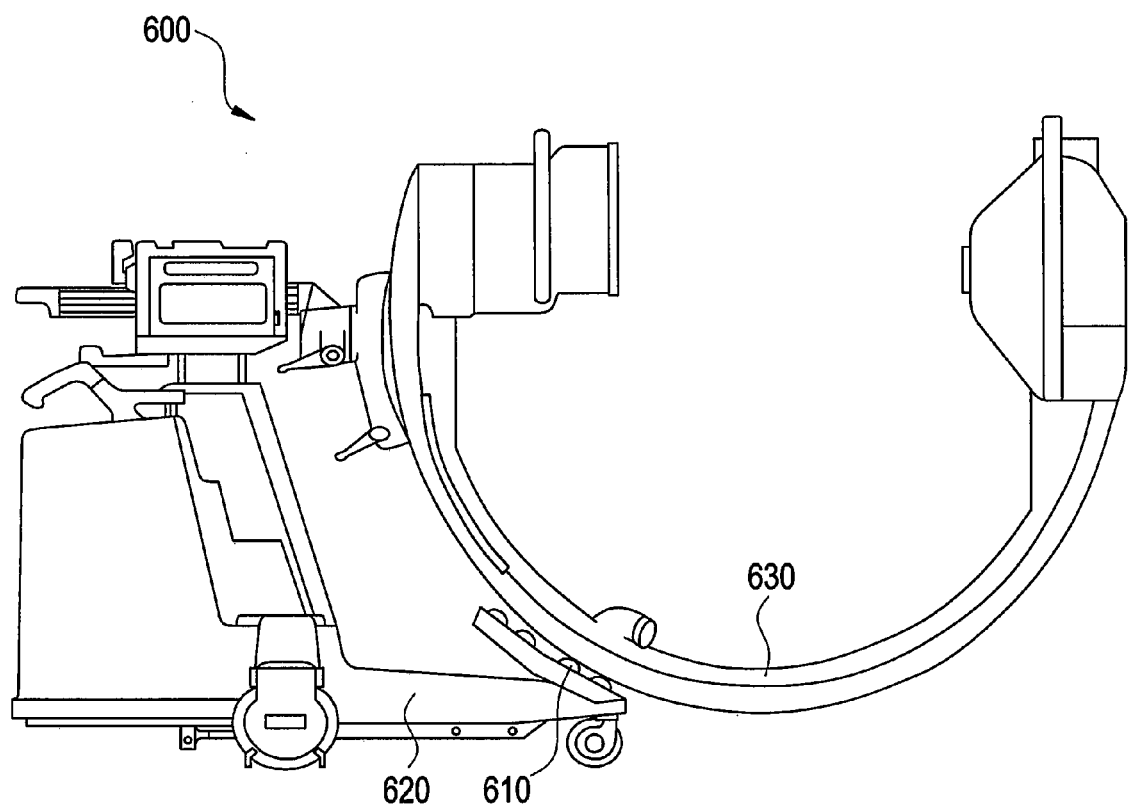
FIG. 7 illustrates a C-arm in a docked, lateral orbital x,y position in accordance with an embodiment of the present invention.
Figure 8:
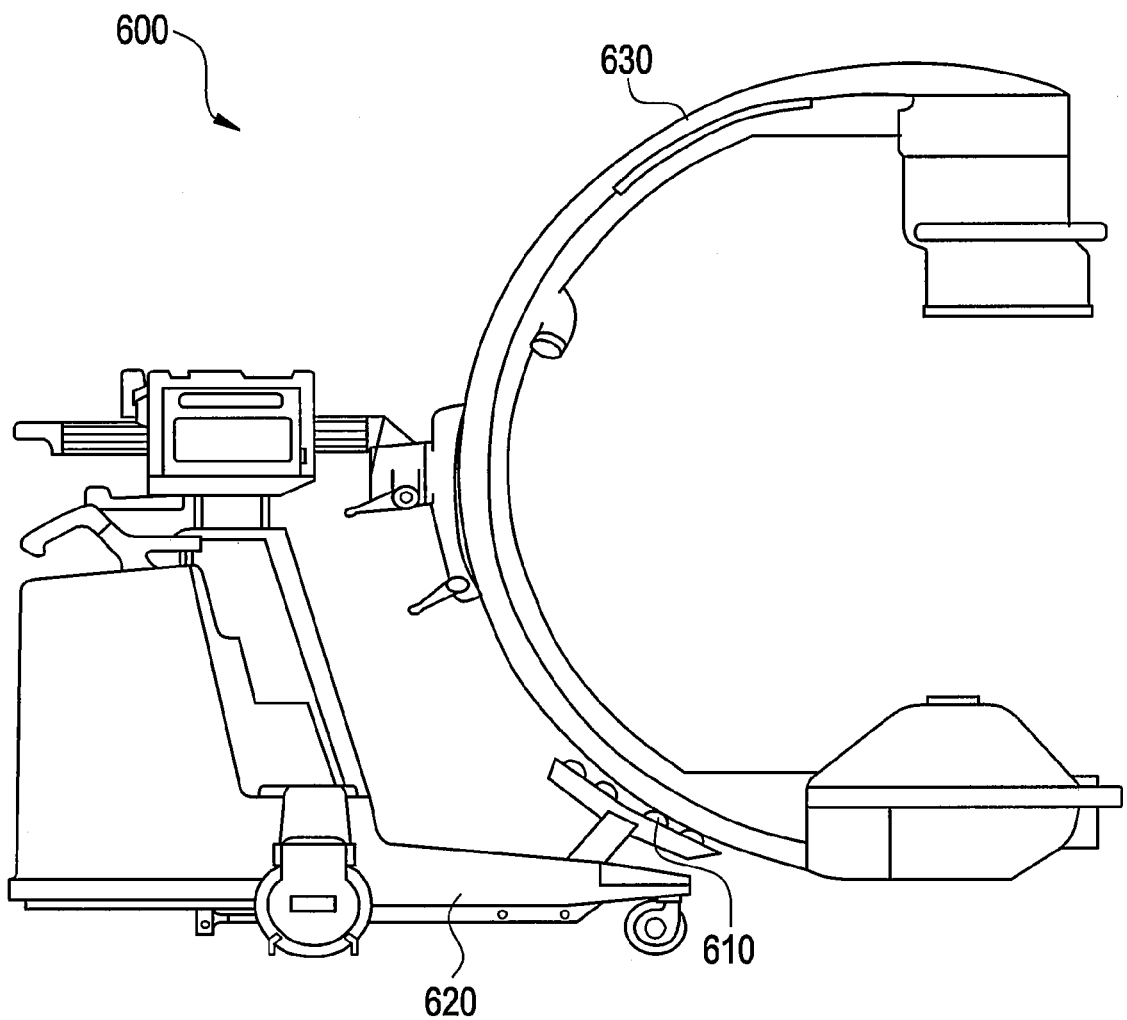
FIG. 8 illustrates an extendable truck assembly in a C-arm system in accordance with an embodiment of the present invention.

Certain embodiments include a truck boom that may be manually or automatically extended to account for lift column elevation and/or cross-arm extension (see FIGS. 7 and 8). FIG. 7 illustrates a C-arm 630 in a docked, lateral orbital x,y position. FIG. 8 illustrates an extendable 'truck' assembly 610 in a C-arm system 600. The truck boom may provide positioning versatility by alleviating a need for a 'home' or 'docking' position. In certain embodiments, a control may be used to retract the boom slightly, as not to interfere with other manual or motorized motions (cross-arm rotation, etc).

Figure 9:
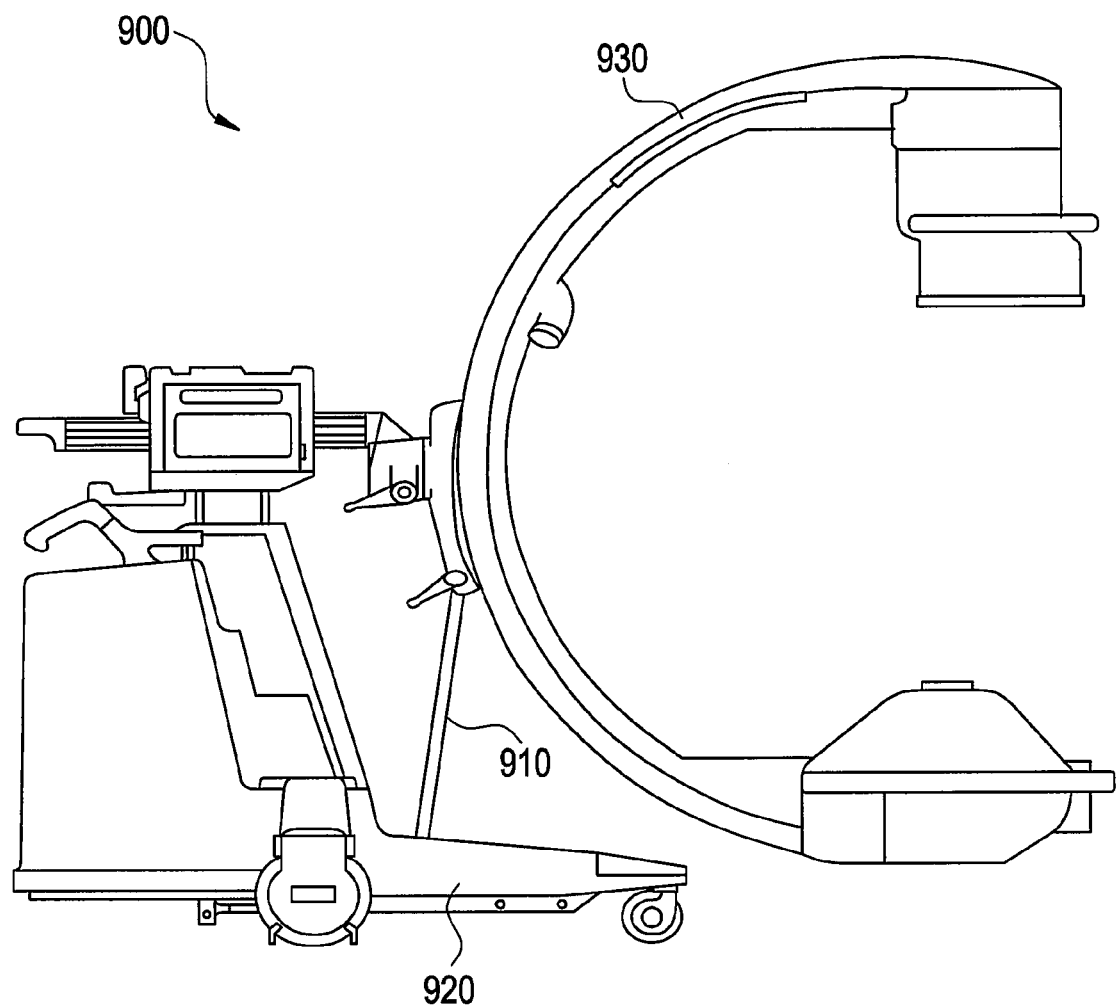
FIG. 9 illustrates a C-capture support positioned on a base in accordance with an embodiment of the present invention.
Figure 10:
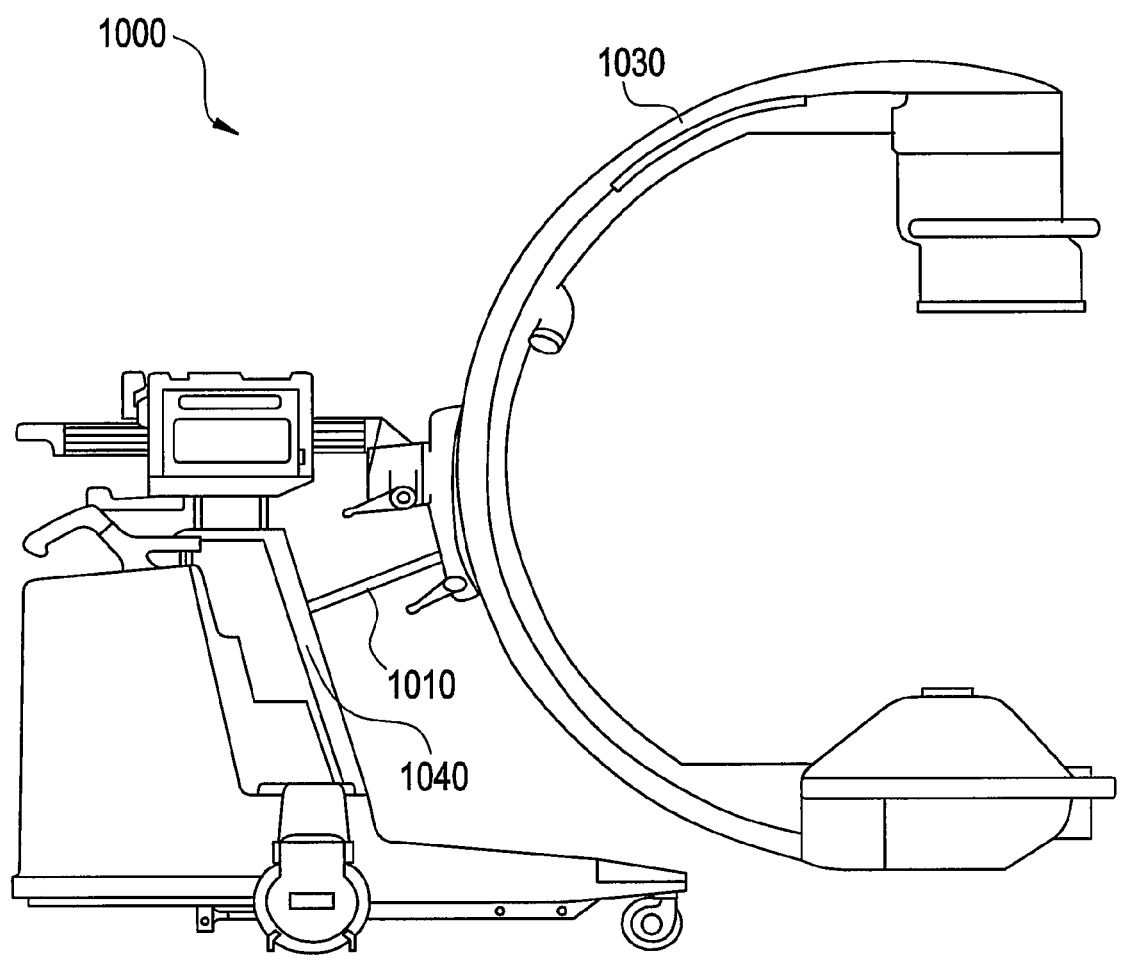
FIG. 10 illustrates a C-capture support positioned on a lift mechanics in accordance with an embodiment of the present invention.

Certain embodiments provide an external linkage between C-capture mechanics and an end of a base (FIG. 9) or lift mechanics (FIG. 10). FIG. 9 illustrates a C-capture support 910 positioned on a base 920 with a C-arm 930. The support 910 may be positioned to contact the C-arm 930, for example. In certain embodiments, the support 910 may be positioned manually and/or via motor and control.

FIG. 10 illustrates a C-capture support 1010 positioned on a lift mechanics 1040. The linkage may be docked on the C-arm system and locked into position, manually and/or automatically, for example, when an orbital scan is to be initiated.

In certain embodiments, use of dampening devices can be incorporated into additional support points in an imaging system. A dampening device helps reduce oscillations due to bumps to the imaging system.

In certain embodiments, unintended gantry motion, such as C-arm flex and oscillations, are irritations inherent to mobile C-arms. In docked mode, gantry flex and oscillation may be significantly reduced during normal imaging, as well as during transport from room to room.

For 2D fluoroscopic navigation, or 'virtual bi-plane', both an AP and a lateral image are acquired and navigated simultaneously. Each image is paired with positional information sampled by the navigation sub-system. The sub-system sampling frequency and response time are not instantaneous, and C-arm oscillations could cause discrepancies between the actual image detector position and the reported image detector position. Gantry stabilization helps reduce oscillation and improve overall navigation accuracy.

By improving positional stability and repeatability of the orbital scan, image quality and accuracy of 3D reconstruction may also be improved. Additionally, when surgical navigation is used, 3D geometric accuracy impacts surgical navigation on an image data set.

FIG. 11 illustrates a flow diagram for a method 1100 for stabilizing an imaging system gantry in accordance with an embodiment of the present invention. At step 1110, a gantry support is provided on a gantry base to provide support for an imaging system gantry arm. For example, a roller, roller assembly, arm and/or other support may be provided to help support or stabilize the gantry arm. The support provides an additional point of contact for the gantry arm at one or more positions in a range of motion of the gantry arm.

At step 1120, the gantry support is positioned with respect to the gantry arm to support the gantry arm along at least a portion of a path of movement of the gantry arm. The gantry arm may be supported in a docked position, for example. The gantry arm may also be supported at a plurality of points along a path of movement of the gantry arm, for example.

At step 1130, the gantry support is extended to contact the gantry arm. The gantry support may be manually and/or automatically extended (e.g., via a motorized control) to contact the gantry arm, for example.

At step 1140, a position of the gantry arm is determined. For example, the gantry arm position may be calculated and/or automatically sensed in order to engage the gantry support with the gantry arm.

Thus, certain embodiments provide a stabilization device positioned on the distal end of a C-arm truck. The stabilization device includes a roller assembly or truck of multiple rollers, for example. The stabilization device may be a fixed and/or extendable device, for example. The stabilization device may be manually engaged and/or motorized, for example. Gantry member position may be calculated and/or automatically sensed (e.g., by proximity, pressure, etc), for example. Certain embodiments may also help dampen oscillations in an imaging system, for example.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A mobile imaging system, said system comprising:
    a variably moveable base, said variably moveable base being moveable along a floor in a plurality of directions;
    a gantry member rotatably attached at one point to said moveable base via an extendable support member from said base, said gantry member including an imaging source; and
    a gantry member stabilization support positioned on or near a distal end of said base for supporting said gantry member during imaging, said gantry member stabilization support contacting said gantry member at at least one point in a range of orbital rotation motion about an axis for said gantry member.

2. The system of claim 1, wherein said gantry member comprises at least one of C-shaped member, an L-shaped member and an O-shaped member.

3. The system of claim 1, wherein said gantry member stabilization support is not permanently attached to said gantry member.

4. The system of claim 1, wherein said gantry member stabilization support comprises a roller support.

5. The system of claim 1, wherein said gantry member stabilization support comprises a truck assembly of multiple rollers.

6. The system of claim 1, wherein said gantry member stabilization support comprises a boom.

7. The system of claim 1, wherein said gantry member stabilization support comprises an imaging assembly capture support.

8. The system of claim 1, wherein said gantry member stabilization support further comprises a dampening device for dampening oscillations due to bumps in the system.

9. The system of claim 1, wherein said gantry member stabilization support comprises at least one of a fixed support and an extendable support.

10. The system of claim 1, wherein said gantry member stabilization support comprises at least one of a manually engaged support and a motorized support.

11. The system of claim 1, wherein said gantry member stabilization support contacts said gantry member to support said gantry member in a docked position.

12. The system of claim 1, further comprising a position sensor for at least one of calculating or automatically sensing a position of said gantry member to engage said gantry member stabilization support.

13. A method for gantry stabilization, said method comprising:
    providing a gantry member stabilization support on or near a distal end of a variably moveable gantry base to provide support for an imaging system gantry member during imaging, said imaging system gantry member moveably attached at one point to said variably moveable gantry base via an extendable support member from said base, said variably moveable gantry base moveable along a floor in a plurality of directions; and
    positioning said gantry member stabilization support with respect to said imaging system gantry member to support said imaging system gantry member along at least a portion of a path of orbital rotation movement about an axis of said imaging system gantry member during imaging.

14. The method of claim 13, wherein said positioning step further comprises extending said gantry member stabilization support to contact said imaging system gantry member.

15. The method of claim 13, further comprising providing support to said imaging system gantry member in a docked position using said gantry member stabilization support.

16. The method of claim 13, further comprising at least one of calculating or automatically sensing a position in the orbital rotational path about an axis of said imaging system gantry member to engage said gantry member stabilization support.

17. An imaging assembly stabilization system, said system comprising:
   an imaging assembly moveably attached at one point to a variably moveable base, said variably moveable base moveable along a floor in a plurality of directions; and
   an imaging assembly support positioned on or near a distal end of said moveable base, said imaging assembly support configured to contact said imaging assembly during imaging to stabilize said imaging assembly at at least one point along an orbital rotational path of said imaging assembly.

18. The system of claim 17, wherein said imaging assembly support comprises at least one of a roller support, a truck assembly of multiple rollers, a boom and an imaging assembly capture support.

* * * * *